United States Patent [19]
Brady

[11] Patent Number: 5,584,304
[45] Date of Patent: Dec. 17, 1996

[54] METHOD OF INSERTING AN IOL USING A FORCEPS INSIDE A FOLDING TUBE

[75] Inventor: Daniel G. Brady, Mission Viejo, Calif.

[73] Assignee: Allergan, Inc., Irvine, Calif.

[21] Appl. No.: 333,099

[22] Filed: Nov. 1, 1994

Related U.S. Application Data

[63] Continuation-in-part of Ser. No. 154,240, Nov. 18, 1993, abandoned, and a continuation-in-part of Ser. No. 235,444, Apr. 29, 1994.

[51] Int. Cl.$^6$ .................................................. A61B 17/00
[52] U.S. Cl. ............................................ 128/898; 606/107
[58] Field of Search ........................... 606/107, 1; 623/4, 623/6; 128/898

[56] References Cited

U.S. PATENT DOCUMENTS

| | | |
|---|---|---|
| 450,266 | 4/1891 | Truax . |
| 2,450,138 | 9/1948 | Harwood . |
| 3,678,927 | 7/1972 | Soichet . |
| 3,703,174 | 11/1972 | Smith . |
| 4,026,281 | 5/1977 | Mayberry et al. . |
| 4,122,556 | 10/1978 | Poler . |
| 4,190,049 | 2/1980 | Hager et al. . |
| 4,198,980 | 4/1980 | Clark . |
| 4,214,585 | 7/1980 | Bailey, Jr. . |
| 4,244,370 | 1/1981 | Furlow et al. . |
| 4,249,271 | 2/1981 | Poler . |
| 4,251,887 | 2/1981 | Anis . |
| 4,253,199 | 3/1981 | Banko . |
| 4,257,521 | 3/1981 | Poler . |
| 4,298,994 | 11/1981 | Clayman . |
| 4,303,268 | 12/1981 | Davidson . |
| 4,325,375 | 4/1982 | Nevyas . |
| 4,373,218 | 2/1983 | Schachar . |
| 4,423,809 | 1/1984 | Mazzocco . |
| 4,446,581 | 5/1984 | Blake . |
| 4,449,257 | 5/1984 | Koeniger . |
| 4,462,404 | 7/1984 | Schwarz et al. . |
| 4,463,457 | 8/1984 | Kelman . |
| 4,468,820 | 9/1984 | Uhler et al. . |
| 4,490,860 | 1/1985 | Rainin . |
| 4,527,294 | 7/1985 | Heslin . |
| 4,573,998 | 3/1986 | Mazzocco . |
| 4,600,004 | 7/1986 | Lopez et al. . |
| 4,619,657 | 10/1986 | Keates et al. . |
| 4,681,102 | 7/1987 | Bartell . |
| 4,715,373 | 12/1987 | Mazzocco et al. . |
| 4,732,150 | 3/1988 | Keener, Jr. . |
| 4,747,404 | 5/1988 | Jampel et al. . |
| 4,759,359 | 7/1988 | Willis et al. . |

(List continued on next page.)

FOREIGN PATENT DOCUMENTS

| | | |
|---|---|---|
| 0270257 | 8/1988 | European Pat. Off. . |
| 0304698 | 8/1989 | European Pat. Off. . |
| 2191439 | 12/1987 | United Kingdom . |
| 8201646 | 5/1982 | WIPO . |
| 8808288 | 11/1988 | WIPO . |
| 9420027 | 9/1994 | WIPO . |

OTHER PUBLICATIONS

Staar Surgical Co. vol. 4, No. 1 Jul. 1988.
Cataract Refract Surg., vol. 15, Mar. 1989, Christ et al.
Folding & Inserting Silicone Intraocular Lens Implants, Faulkner, Nov. 1987.
Microsert II™, Model IM002, Directions for Use with the Chiroflex™II, Chiron IntraOptics, Jul., 1993.
IOL & Ocular Surgery News, vol. 1, No. 14 (Jul. 1983).

*Primary Examiner*—Stephen C. Pellegrino
*Assistant Examiner*—Glenn Dawson
*Attorney, Agent, or Firm*—Frank J. Uxa

[57] ABSTRACT

Methods and apparatus for inserting foldable IOL's into the eye are disclosed. The present methods include holding a foldable IOL with a forceps; passing the IOL through the bore of a tubular member; placing the distal end portion of the tubular member in proximity to or in the eye; causing at least a portion of the IOL to pass through the open distal end of the tubular member; and releasing the IOL from the forceps in the eye. Apparatus including tubular members and forceps, particularly useful in practicing the present methods, are also disclosed.

12 Claims, 2 Drawing Sheets

U.S. PATENT DOCUMENTS

| | | |
|---|---|---|
| 4,763,650 | 8/1988 | Hauser . |
| 4,765,329 | 8/1988 | Cumming et al. . |
| 4,769,034 | 9/1988 | Poley . |
| 4,781,719 | 11/1988 | Kelman . |
| 4,785,810 | 11/1988 | Baccala et al. . |
| 4,791,924 | 12/1988 | Kelman . |
| 4,813,957 | 3/1989 | McDonald . |
| 4,819,631 | 4/1989 | Poley . |
| 4,834,094 | 5/1989 | Patton et al. ............... 623/6 |
| 4,836,201 | 6/1989 | Patton et al. . |
| 4,844,065 | 7/1989 | Faulkner . |
| 4,844,093 | 7/1989 | Jampel et al. . |
| 4,880,000 | 11/1989 | Holmes et al. . |
| 4,917,680 | 4/1990 | Poley . |
| 4,919,130 | 4/1990 | Stoy et al. . |
| 4,934,363 | 6/1990 | Smith et al. . |
| 4,976,716 | 12/1990 | Cumming . |
| 4,988,352 | 1/1991 | Poley . |
| 5,098,439 | 3/1992 | Hill et al. . |
| 5,123,905 | 6/1992 | Kelman . |
| 5,190,552 | 3/1993 | Kelman . |
| 5,260,021 | 11/1993 | Zeleznick . |
| 5,275,604 | 1/1994 | Rheinish et al. . |

U.S. Patent     Dec. 17, 1996     Sheet 1 of 2     5,584,304
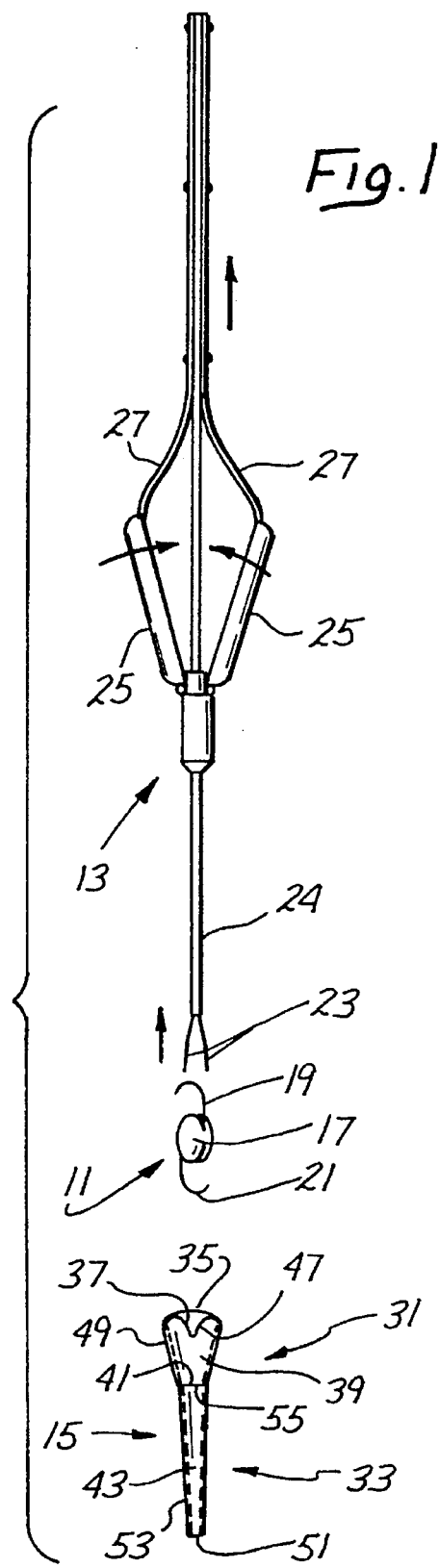
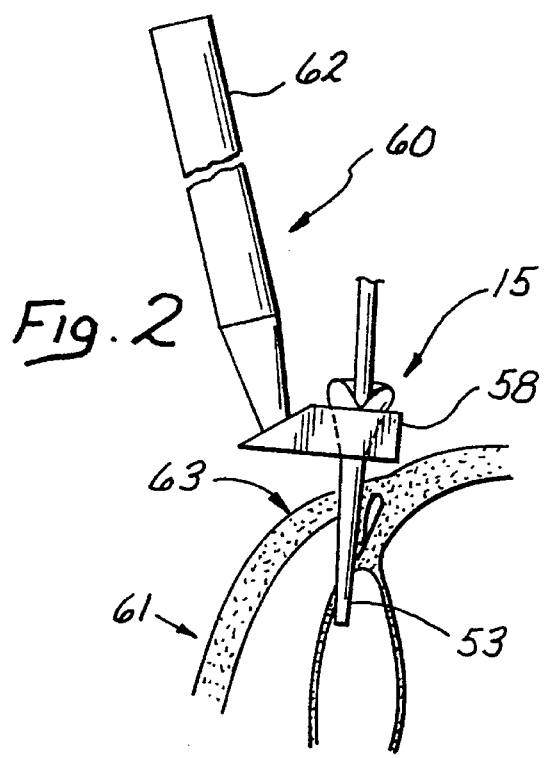
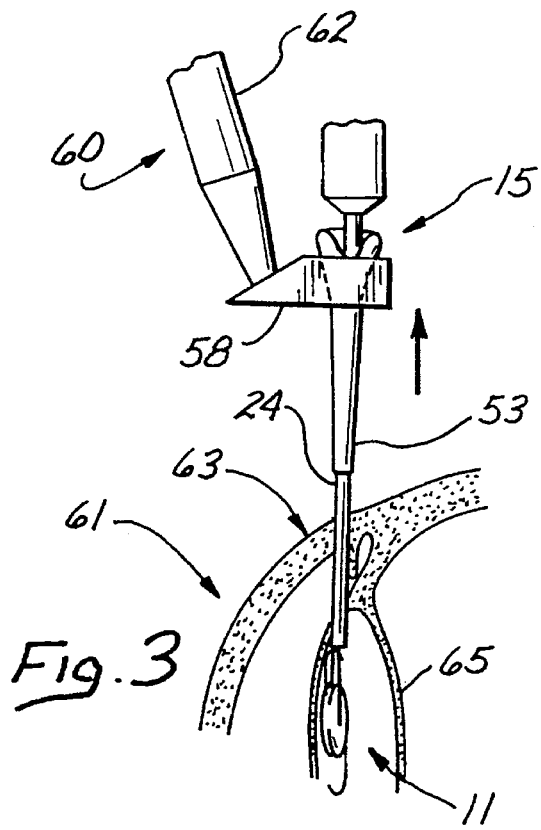

1

METHOD OF INSERTING AN IOL USING A FORCEPS INSIDE A FOLDING TUBE

RELATED APPLICATIONS

This application is a continuation-in-part of application Ser. No. 08/154,240 filed Nov. 18, 1993, now abandoned, and of Ser. No. 08/235,444 filed Apr. 29, 1994, pending. The disclosure of each of these applications is incorporated in its entirety herein by reference.

FIELD OF THE INVENTION

This invention relates to a method and apparatus for inserting a foldable intraocular lens (IOL) into the eye of a patient.

BACKGROUND OF THE INVENTION

As is well known, an IOL is used to replace the natural lens of the human eye when the natural lens becomes incapable of functioning as desired. A typical IOL includes an optic or lens and one or more fixation members for fixing the IOL in the desired position within the eye.

The optic of an IOL may be constructed of hard, nondeformable materials such as polymethylmethacrylate or of soft, deformable materials such as silicone based or acrylic based materials. One advantage of the deformable IOL's is that they can be deformed into a configuration which permits them to be inserted through a smaller incision into the eye.

In deforming the IOL, the optic is typically folded in a way to cause the IOL to have smaller dimensions which enables it to be inserted through a smaller incision. An IOL which is deformed by forming it into a roll is also folded in the sense that the roll constitutes at least one fold. As used herein, a folded optic, folded IOL and folded condition have reference to an optic which is deformed in any manner, including rolling, that produces a fold.

It is desirable to compactly fold a foldable IOL because this can minimize the length of the incision necessary to insert the folded IOL into the eye. However, because IOL's are very small, they are difficult to grasp and even more difficult to fold into an efficient, compact configuration of minimal dimensions. As an example of size, the optic of a foldable IOL may be in the neighborhood of about 5 to about 7 millimeters in diameter.

Various devices have been proposed for use in folding a foldable IOL. For example, a forceps can be used to provide a single fold in an IOL which, in effect, folds the IOL in half. This, however, is not a configuration which in general will minimize the length or size of the incision needed for insertion of the IOL into the eye. Mazzocco U.S. Pat. No. 4,573,998 discloses forceps of a particular configuration for use in conjunction with other devices which apparently provide multiple folds in an IOL. However, this patent does not disclose how the folds are initially formed in the IOL. Also, this patent does not disclose the use of a forceps in the eye to facilitate the insertion of a foldable IOL.

SUMMARY OF THE INVENTION

This invention provides a method for inserting a foldable IOL into the eye of a patient which generally overcomes the disadvantages identified above. With this invention, the folded IOL can be relatively easily, safely and controllably inserted into the eye of the patient through a small incision. In addition, the IOL can be efficiently, compactly and relatively easily folded into a folded condition for insertion in the eye.

In one broad aspect of the invention, methods of inserting foldable IOL's into the eye of a patient are provided. Such methods include holding a foldable IOL with a forceps. The foldable IOL can be in a folded condition, a partially folded condition or an unfolded condition at this point. The held foldable IOL is passed distally through the bore or lumen of a tubular member which has a distal end portion and an open distal end. When the foldable IOL is located in that portion of the bore or lumen defined by the distal end portion of the tubular member, the foldable IOL is preferably already folded, for example, in substantially the final folded condition or configuration for inserting into the eye of the patient. At this point, the foldable IOL is held by the forceps, which preferably enters the tubular member proximally.

The distal end portion of the tubular member is placed in proximity to or in the eye of the patient, preferably substantially abutting or through a relatively small incision, more preferably no larger than about 3.2 mm or about 3.0 mm and still more preferably no larger than about 2.8 mm. For example, the incision may be through the sclera or through the cornea.

At least a portion of the foldable IOL, preferably substantially all of the optic and more preferably substantially all of the IOL, is caused to pass through the open distal end of the tubular member. The foldable IOL is released from the forceps in the eye of the patient. This releasing step is preferably accomplished at a location in the eye at which the IOL can be conveniently positioned for use, for example, in the anterior chamber or posterior chamber, as desired. The use of a forceps to hold the IOL in the distal end portion of the tubular member which is located in proximity to or in the eye provides for controlled placement of the IOL in the eye. Also, since the forceps is holding or carrying the IOL, a positive, easily controlled force on the forceps or on the tubular member causes the IOL to exit the distal end opening of the tubular member in a readily controlled manner. The tubular member itself is important since it protects the IOL and insures that it is maintained in the desired folded condition. Also, when the tubular member is located in the eye, it protects the incision against undue risk of tearing. In short, the present methods provide for safe, effective and controlled insertion of foldable IOLs into the eyes of patients.

The foldable IOL can be in an unfolded state, a partially folded state or in the final folded state or conditions prior to being introduced into the tubular member. Thus, for example, the tubular member can be constructed to receive an unfolded, partially folded or fully folded IOL. If the foldable IOL is unfolded or only partially folded prior to being introduced into the bore of the tubular member, the tubular member itself is preferably structured and adapted to facilitate the folding or further folding of the IOL as the IOL is introduced into and/or passes through the bore. The tubular member, for example, the distal end portion of the tubular member, is preferably sized and adapted to maintain the IOL located in the bore, for example, that portion of the bore defined by the distal end portion, in the desired folded state.

The IOL held by the forceps prior to being introduced into the bore of the tubular member may be at least partially folded, for example, the optic of the IOL being folded in half.

In the event that the foldable IOL is in an unfolded condition or partially folded condition prior to being introduced into the bore of the tubular member, it is preferred that the folding or further folding of the IOL occur while the IOL is being held by the forceps.

In a particularly useful embodiment, the distal end portion of the tubular member is passed into the eye and at least a part, for example, substantially all or only a part, of the distal end portion is withdrawn from the eye of the patient prior to releasing the foldable IOL from the forceps in the eye. This step of withdrawing at least a portion of the tubular member from the eye before releasing the IOL enhances the safety of, for example, reduces the risk of injury to the eye caused by, inserting the IOL into the eye. Such withdrawing directs the force away from the eye, thereby reducing the risk of the tubular member or forceps being forced deeper in the eye when the IOL is released in the eye.

While the tubular member is withdrawn from the eye, it is preferred that the forceps holding the IOL be maintained substantially stationary relative to the eye. Thus, as the tubular member is withdrawn, the stationary held. IOL passes through the open distal end of the tubular member. However, because the held IOL is stationary relative to the eye, there is no movement of the forceps further into the eye. Along with the enhanced safety of this approach, substantial precision in the placement or positioning of the IOL in the eye is achieved.

Alternatively, the tubular member can be held stationary relative to the eye and the forceps moved forwardly so that the held IOL passes through the open distal end of the stationary tubular member for release in the eye. Care should be exercised to control the forward movement of the forceps to properly place the IOL in the eye and to avoid damaging the eye.

In another broad aspect of the present invention, apparatus or inserters for inserting a foldable intraocular lens into an eye of a patient are provided. The methods for inserting a foldable IOL into the eye of a patient described herein can be, and preferably are, practiced using the present apparatus. In general, the present inserters comprise a tubular member and a forceps. The tubular member has a bore, a distal end portion, an open proximal end and an open distal end. The bore is sized and adapted to receive a foldable IOL and to hold or maintain the IOL in a folded state. The distal end portion of the tubular member is sized and adapted to be placed in proximity to or in the eye of the patient. The forceps are sized and adapted to hold the foldable IOL as the IOL passes distally through the bore and into the distal end portion of the tubular member.

The tubular member is preferably sized and adapted to facilitate folding the foldable IOL into a folded state. In a particularly useful embodiment, the tubular member, for example, the bore of the tubular member, is tapered so as to have a generally decreasing cross-sectional area proximally to distally. In this embodiment, the IOL preferably becomes more compactly folded as the IOL is passed distally in the bore of the tubular member. The distal end portion of the tubular member is preferably sized and adapted to be placed in the eye of the patient through an incision no larger than about 3.2 mm, more preferably no larger than about 3.0 mm and still more preferably no larger than about 2.8 mm, in size.

The forceps of the present invention may have any suitable size and configuration, provided that such forceps functions as described herein without causing undue damage to the IOL being inserted or to the patient in whose eye the IOL is being inserted. In general, a forceps as used herein is a component which includes two or more elements one or more of which are moveable relative to another of the elements so as to hold a foldable IOL between such elements and to release such IOL from such holding action, as desired. The forceps can be manually or automatically operated, can be mechanically and/or electrically and/or pneumatically and/or otherwise powered, and can be passed freely distally through the tubular member or by the use of threaded components or other screw-type systems to control the proximal-distal motion of the forceps.

A very useful preferred feature of the present inserters is a folder assembly which is operatively coupled to, for example, secured to or integrally formed with, the tubular member. The folder assembly is preferably located proximally of the tubular member. The folder assembly is effective to fold the foldable IOL into a desired folded state prior to introducing the foldable IOL into the bore of the tubular member through the open proximal end of the tubular member. The folder assembly can have any suitable size and configuration provided that it functions as described herein and has no substantial or undue detrimental effect on the IOL being inserted or on the patient in whose eye the IOL is being inserted. The folder assembly, in one embodiment, comprises a loading chamber having a proximal end, and preferably a distally extending opening. The loading chamber further defines a lumen or bore which is substantially aligned with the bore of the tubular member. The loading chamber is adapted to receive a foldable IOL held by a forceps in an unfolded state at the distally extending opening and to fold the IOL and maintain the IOL folded as the IOL is placed in the lumen.

In another embodiment, the folder assembly includes a first element and a second element which are moveable, for example, hingeably moveable, relative to each other to cause the folder assembly to be configured in an open position or in a closed position. Thus, with the folder assembly in the open position, the foldable IOL held by the forceps is placed in the folder assembly so that the held IOL is folded as the first and second elements are moved relative to each other to configure the folder assembly in the closed position. The folded IOL, still held by the forceps, is then passed distally into the bore of the tubular member which is aligned with the lumen formed by the folder assembly in the closed position in which the folded IOL is located.

The present inserters preferably include a hand grip which is operatively coupled to, for example, integrally formed with, the tubular member, and is sized and adapted to be held by the hand (or hands) of a human (surgeon) to move the tubular member relative to the eye of the patient. The inclusion of such a hand grip effectively facilitates manipulation of the lens inserter by the surgeon in and around the eye of the patient. The ability to so manipulate the inserter increases the ease with which the IOL can be properly placed or positioned in the eye and reduces the risk of damaging the eye. The hand grip included in the present inserters can be of any suitable configuration provided that it functions as described herein and has no undue or significant detrimental effect on the IOL being inserted or on the patient.

The foldable IOL's insertable in the eye using the present methods and apparatus may be of any configuration suitable to perform the desired function in the eye. Such lenses often include a lens body or optic which has optical properties in the eye. Such lens body is foldable as set forth herein. In many instances, the lens body is generally circular. However, other configurations are also useful. In addition, IOL's may, and preferably do, include at least one flexible fixation member which is secured or attached to the optic. This flexible fixation member acts to fix the IOL in position in the eye. Examples of flexible fixation members include flexible haptics which are preferably radially resilient and extend outwardly from the periphery of the lens body. Specific examples of such flexible haptics include plate haptics and those commonly known as J-loops and C-loops. Such haptics engage appropriate circumferential eye tissue adjacent the iris or within the capsular bag to fix the lens in position in the eye. A very useful IOL includes a plurality of, especially two, such flexible haptics.

The lens body may be made of any suitable material such as polymethylmethacrylate, silicone, hydrogel or other well known materials for foldable IOL construction. Preferably the optic also includes an ultraviolet light absorber. The flexible fixation member or members may be made of any suitable material such as polymethylmethacrylate, prolene, polypropylene, nylon, silicone or other materials suitable for implantation into the eye.

As used herein, the terms "foldable" and "deformable" mean that an IOL, and in particular the lens body or optic of an IOL, can be temporarily reshaped so as to pass through a smaller incision relative to the incision required if the IOL was not temporarily reshaped.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a plan view illustrating forceps, a first form of tubular member and a foldable IOL.

FIG. 2 is a side elevational view illustrating one technique for placing the distal end portion of a tubular member in the eye of a patient.

FIG. 3 is a side elevational view illustrating one technique for withdrawing the distal end portion of a tubular member from the eye of a patient.

DETAILED DESCRIPTION OF THE DRAWINGS

Figure 4:
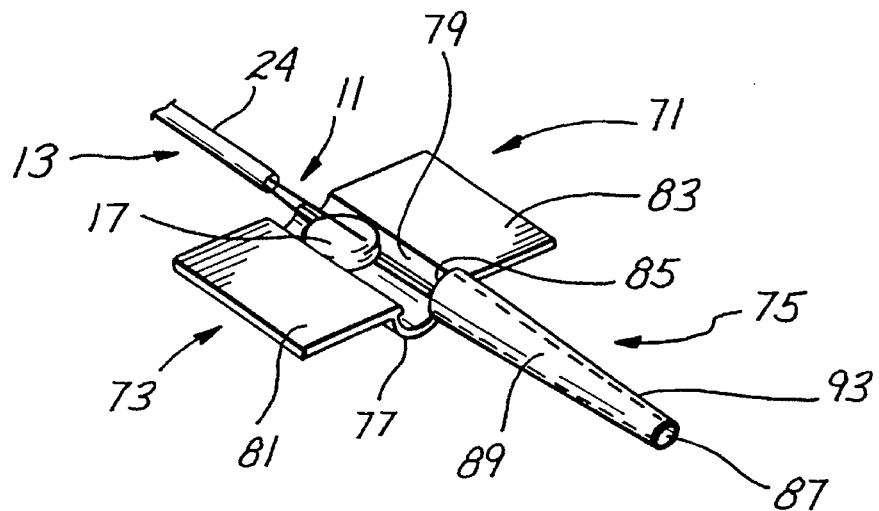
FIG. 4 is a perspective view illustrating the forceps and unfolded IOL in combination with a second form of tubular member.

FIG. 1 shows an IOL 11 which can be held by forceps 13 and placed into a tubular member 15. Both the IOL 11 and the forceps 13 may be of conventional construction. The IOL 11 comprises an optic 17 of foldable or deformable material, such as silicone based or acrylic based material and identical fixation members 19 and 21 coupled to the optic. The optic 17 can be folded from the normal configuration shown in FIG. 1 and is sufficiently resilient and has sufficient memory such that upon insertion into the eye, it recovers to its normal configuration. In the form shown in FIG. 1, the fixation members 19 and 21 each include a resilient strand of a suitable resilient material, such as polypropylene or polymethylmethacrylate, and these members are used to fix or retain the IOL 11 in the eye following implantation. The particular form of the IOL shown in FIG. 1 is purely illustrative.

The forceps 13 includes arms 23 which extend out of tube 24 and can be moved between an open position of FIG. 1 in which the arms are spaced apart and a closed position in which the arms are moved toward each other by levers 25. The levers 25 are normally held apart by springs 27 such that the arms 23 are normally spring biased to the open position. However, by moving the levers 25 toward each other, the arms 23 are likewise moved toward each other to a closed position. Forceps of this type can be purchased from Back-Mueller Inc. of St. Louis, Mo. Of course, forceps of other kinds and configurations may be employed.

Tubular member 14 includes a loading chamber 31 and an injection portion 33.

Loading chamber 31 includes a proximal end 35, a distally extending proximal end opening 37 and a first lumen 39 (illustrated by dashed lines). This first lumen 39 extends from the distally extending proximal end opening 37 to the distal end 41 of loading chamber 31 and is contiguous with second lumen 43 (illustrated by dashed lines) defined by injection portion 33. The cross-sections of loading chamber 31 and of first lumen 39 are tapered and decrease from the proximal end 35 to the distal end 41 of the loading chamber. The distally extending proximal end opening 37, which is non-circular, is partially defined by a generally V-shaped through notch 47 which is formed in the sidewall 49 of loading chamber 31.

Injection portion 33 includes a distal end opening 51 which is generally elliptical in cross-section, although other configurations, such as a circular cross-section, may be employed, and has a distal end portion 53. The cross-sections of injection portion 33 and second lumen 43 taper and decrease gradually from the proximal end 55 to the distal end opening 51 of the injection portion.

Tubular member 15 is made, for example, molded, as a single or unitary structure which terminates proximally at the proximal end 35 of loading chamber 31. Although the tubular member 15 (as well as the other tubular member embodiments or forms illustrated herein) can be made of any suitable material of construction, a preferred material is a transparent polymeric material, such as polypropylene. The use of a transparent material is advantageous in that the exact location in tubular member 15 of the IOL to be inserted is more readily ascertained by looking through apparatus 10. The tubular member 15 (as well as the other tubular member embodiments or forms illustrated herein) is preferably made of a biocompatible material so as to cause no undue detrimental effect on the eye into which the injection portion 33 is placed. The tubular member 15 (as well as the other tubular member embodiments or forms illustrated herein) may be made of a sterilizable material so that it can be conveniently reused, for example, many times. Examples of sterilizable materials from which tubular member 15 can be made include metals, such as stainless steel, titanium and the like.

The distally extending proximal end opening 37 of loading chamber 31 is configured to facilitate the folding of an IOL as it passes through this opening into the first lumen 39. In addition, the distal tapering of first lumen 39 assists in effecting and maintaining a controlled folding of an IOL passing therethrough. The IOL 11 can be unfolded, partially folded or even fully folded at the time it is passed into first lumen 39.

Tubular member 15 is sized and configured to fold an IOL carried by forceps 11 passing through the distally extending proximal end opening 37 of loading chamber 31 into the first lumen 39. The folded IOL, still being held and carried by forceps 13, is passed from the loading chamber 31 into the distal end portion 53 of injection portion 33.

Forceps 13 is used to pull (or carry) the folded IOL through the second lumen 43 and out of the distal opening 51 of injection portion 33. Forceps 13 enters the tubular member 15 proximally. The forceps 13 releases the IOL 11 after at least a portion of the IOL exists the second lumen.

The inserter system illustrated in FIG. 1 operates as follows. When it is desired to insert IOL 11 into an eye, the IOL, preferably, in the unfolded state, is grasped by a forceps 13. Tubular member 15, which (along with forceps 13) is typically packaged in sterile condition, is removed from its packaging and is ready for use. With IOL 11 in the grasp of forceps 13, the surgeon can make a final inspection of the IOL, for example, for structural damage. A lubricant, such as sodium hyaluronate and the like ophthalmically acceptable lubricants, may be applied to IOL 11 and/or the first lumen 39 and second lumen 43 to facilitate the passing of the IOL into and through the first and second lumens.

IOL 11, grasped or held by forceps 13, is passed through distally extending proximal end opening 37 into the first lumen 39 of loading chamber 31. This passing causes the optic 17 of IOL 11 to fold upon itself so that it conveniently fits in the first lumen 39. The IOL 11, still in the grasp of forceps 13 is carried distally through first lumen 39 and second lumen 43 to the distal end portion 53 of the injection portion 33. IOL 11 is now ready to be inserted into an eye.

Referring now to FIGS. 2 and 3, the IOL 11 is to be placed in eye 61 into an area formerly occupied by the natural lens of the eye. FIGS. 2 and 3 show the sclera 63 of the eye 61 having an incision through which the distal end portion 53 of injection portion 33 may be inserted. Alternatively, the incision can be made through the cornea. The tubular member 15 is removably secured to one end 58 of a hand tool 60 so that the surgeon, holding the handle or housing 62 of the hand tool, can conveniently manipulate tubular member 15, for example, in eye 61. Distal end portion 53 has a sufficiently small cross-section to pass into the eye 61 through a 3.0 mm incision in the sclera 63.

The injection portion 33 is manipulated within eye 61 until it is positioned so that IOL 11 can be properly positioned in eye 61, that is in the anterior chamber, the posterior chamber, the capsular bag 65 or in the sulcus, after being released. Thus, the surgeon is able to controllably position injection portion 33, with IOL 11 in the distal end portion 53 thereof, before releasing the IOL. Once injection portion 33 is so positioned, the tubular member 15 is withdrawn proximally from the eye while the forceps 13 is maintained stationary relative to the eye. A portion of tube 24 and arms 23 of forceps 13 remain in eye 61. The forceps 13 is then moved to the open position to release IOL 11 in the eye. The forceps 13 is then withdrawn from the IOL 11, placed in the closed position and withdrawn from the eye 61. If needed, the position of IOL 11 can be adjusted by the forceps 13 or by a small, bent needle or similar tool inserted into the same incision.

Alternately, the tubular member 15 is positioned so that the distal end opening 51 is directly over the incision and distal end portion 53 abuts the surface of eye 61. Once tubular member 15 is so positioned, the forceps 13 holding the folded IOL 11 is passed through distal end opening 51 and the incision into the eye 61. The forceps 13 is manipulated in the eye 61 to the proper position for IOL 11 to be released. Once this positioning has occurred, the forceps 13 is moved to the open position to release IOL 11 in the eye. The forceps 13 are then withdrawn from the IOL 11, placed in the closed position and withdrawn from the eye. Tubular member 15 is then removed from the surface of the eye. If needed, the position of IOL 11 can be adjusted by forceps 13 or by a small, bent needle or similar tool inserted into the same incision.

Once the IOL 11 is properly placed in eye 61 and forceps 13 is withdrawn from the eye, the incision in the sclera 52 may be mended, for example, using conventional techniques. After use, tubular member 15 is preferably disposed of.

If the incision is made in the cornea of eye 61 and distal end portion 53 is placed or passed into the eye, it is preferred that the distal end portion of injection portion 33 be only partially withdrawn from the eye. Thus, distal end portion 53 is withdrawn from the eye sufficiently to expose IOL 11 which remains held by forceps 13. Once forceps 13 releases IOL 11 in the eye, the forceps is placed in the closed position and moved back into the distal end portion 53 of injection portion 33 and then tubular member 15 is removed in its entirety from eye 61.

Figure 5:
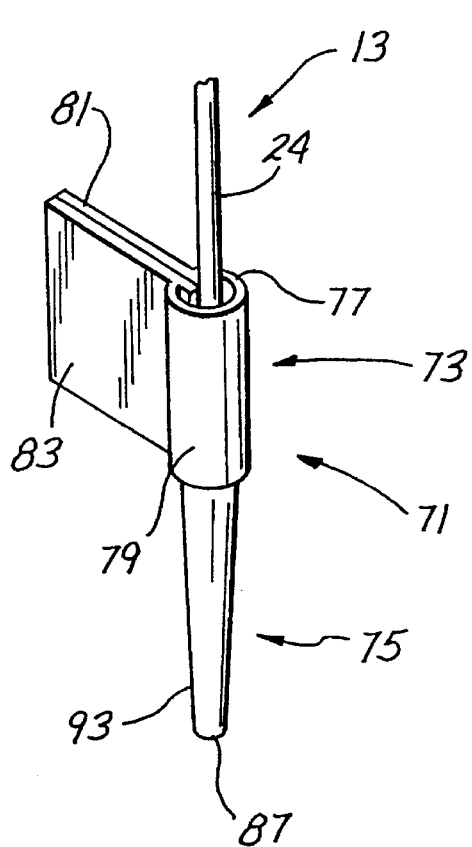
FIG. 5 is a perspective view illustrating the second form of tubular member loaded with the folded IOL.

FIGS. 4 and 5 illustrate an alternate inserter assembly for use in combination with forceps 13 to insert IOL 11 into eye 61. This inserter assembly, shown generally at 71, is a combination lens folder and inserter, and includes a proximal folder portion 73 and an injection tube 75.

Folder portion 73 includes first and second folder elements 77 and 79 which are integrally formed with wing members 81 and 83. First and second folder elements 77 and 79 are hingeably moveable relative to each other between an open position (shown in FIG. 4) and a closed position (shown in FIG. 5). Injection tube 75 includes a proximal opening 85, a distal opening 87 and a lumen 89 (illustrated by dashed lines) therebetween. The injection tube 75 and lumen 89 are both tapered with the proximal end having a larger cross-sectional area than the distal end. Injection tube 75 includes a distal end portion 93 located adjacent distal opening 87.

Inserter assembly 71 operates as follows. When it is desired to insert IOL 11 into the eye, it is placed between first and second folder elements 77 and 79 as shown in FIG. 4. The optic 17 of IOL 11, which is held by forceps 13, is unfolded at this point. Alternately, the IOL 11, held by forceps 13, can be placed between the first and second folder elements 77 and 79 in a partially folded condition or even in the fully or final folded condition. First and second elements 77 and 79 are then hingeably moved together into the closed position, as shown in FIG. 5. Throughout this movement, IOL 11 is held by forceps 13. Bringing first and second folder elements 77 and 79 together causes the optic 17 of IOL 11 to fold. In the closed position, the first and second folder elements 77 and 79 maintain the IOL 11 in a folded state. Thus, if the IOL 11 is fully folded prior to being placed between the first and second folder elements 77 and 79 in the open position, such folder elements in the closed position act to maintain the IOL 11 in a folded state. In addition, wing members 81 and 83 act as a hand grip which the surgeon can hold in manipulating inserter assembly 71.

With forceps 13 continuing to hold folded IOL 11, the IOL is moved into lumen 89 distally and is passed into the distal end portion 93 of the inserter tube 75. At this point, IOL 11 is ready to be inserted into the eye.

As discussed with regard to the embodiment shown in FIGS. 2 and 3, a similar incision is made in the sclera of the eye. The injection tube 75 is placed in the incision and is passed to the point where it is desired to position IOL 11. At this point, injection tube 75 is withdrawn proximally from the incision in the eye, while maintaining the IOL 11 and forceps 13 substantially stationary relative to the eye. This withdrawal causes the IOL 11 to pass through the distal opening 87 of inserter tube 75. The forceps 13 is caused to move into the open position to release the IOL 11 from the forceps. The forceps 13 is then withdrawn from the IOL 11, placed in the closed position and withdrawn from the eye through the incision. If needed, the IOL 11 can be positioned in the eye, as discussed previously.

Alternately, in a manner similar to that discussed previously, the distal opening 87 can be placed over the incision with distal end portion 93 in abutting relationship to the surface of the eye. Once injection tube 75 is so positioned, the forceps 13 holding the folded IOL 11 is passed through distal opening 87 and the incision into the eye. The forceps 13 is manipulated in the eye to the proper position for IOL 11 to be released. Once this positioning has occurred, the forceps 13 is moved to the open position to release IOL 11 in the eye. The forceps 13 are then withdrawn from the IOL 11, placed in the closed position and withdrawn from the eye. Injection tube 75 is then removed from the surface of the eye. If needed, the IOL 11 can be positioned in the eye as discussed previously.

After proper positioning of IOL 11 and the forceps 13 has been withdrawn from the eye, the incision may be mended, as described previously. After use, the inserter assembly 71 is preferably disposed of.

Figure 6:
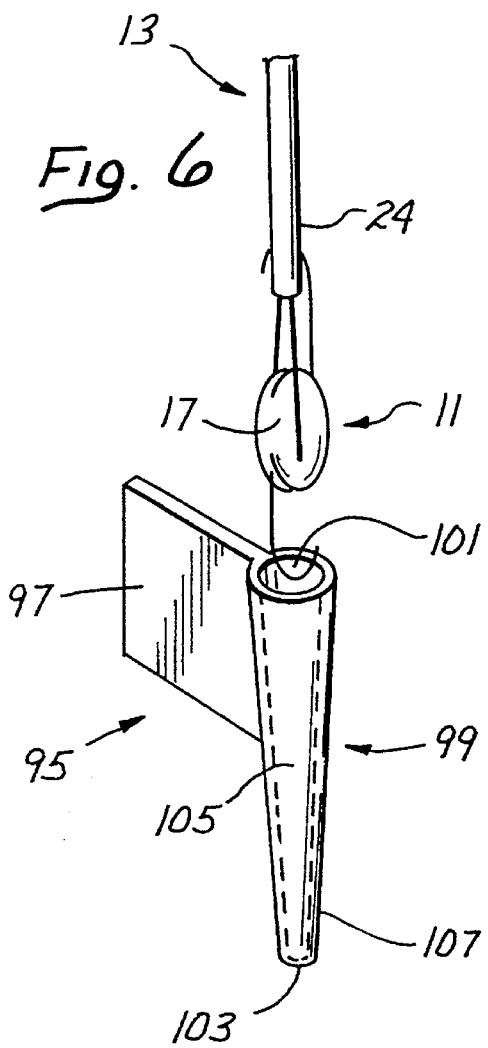
FIG. 6 is a perspective view illustrating the forceps and unfolded IOL in combination with a third form of tubular member

A further embodiment of a folder-inserter combination is shown in FIG. 6. This combination, shown generally at 95, includes a hand grip wing 97 and a tubular portion 99.

Tubular portion 99 includes an open proximal opening 101 and a distal opening 103 with a lumen 105 (illustrated by dashed lines) passing therebetween. The tubular potion 99 and lumen 105 are tapered with larger cross-sectional areas at the proximal ends than at the distal ends. Tubular portion 99 further includes a distal end portion 107. The hand grip wing 97, which is integrally formed with tubular potion 99, is sized to be held by the surgeon in manipulating combination 95.

Combination 95 operates as follows. When it is desired to insert IOL 11 into an eye, it is grasped or held by forceps 13, as shown in FIG. 6. With IOL 11 being held by forceps 13, it is passed through proximal opening 101 into lumen 105. In so doing, the optic 17 of IOL 11 folds into a more compact condition. As the held IOL 11 passes distally further into lumen 105, the folding of optic 17 becomes more compact. The held IOL 11 is passed into the distal end portion 107. At this point, IOL 11 is ready to be inserted into the eye.

As described previously with regard to the embodiment shown in FIGS. 2 and 3, a similar incision is made in the sclera of the eye. The surgeon grasps the hand grip wing 97 to manipulate the distal end portion 107 into proper position in the eye for releasing IOL 11. Once this positioning is accomplished, the distal end portion 107 is removed from the incision while maintaining the IOL 11 and forceps 13 substantially stationary relative to the eye. This causes the IOL 11 to pass through the distal opening 103 of tubular portion 99. After the IOL 11 has passed through the distal opening 103, the forceps is moved to the open position, thereby releasing IOL 11 in the eye. The forceps 13 is then withdrawn from the IOL 11, placed in the closed position and withdrawn from the eye. The IOL 11 can be repositioned in the eye as described previously.

Alternately, the tubular portion 99 is positioned so that the distal opening 103 is directly over the incision and distal end portion 107 abuts the surface of the eye. Once tubular portion 99 is so positioned, the forceps 13 holding the folded IOL 11 is passed through distal opening 103 and the incision into the eye. The forceps 13 is manipulated in the eye to the proper position for the IOL 11 to be released. Once this positioning has occurred, the forceps 13 is moved to the open position to release IOL 11 in the eye. The forceps 13 are then withdrawn from the IOL 11, placed in the closed position and withdrawn from the eye. Tubular portion 99 is then removed from the surface of the eye. If needed, the position of IOL 11 can be adjusted by forceps 13 or by a small, bent needle or similar tool inserted into the same incision.

Once the IOL is properly positioned in the eye and the forceps is withdrawn from the eye, the incision may be mended, as described previously. After use, the combination 95 is preferably disposed of.

The present IOL insertion methods and apparatus are straightforward and easy to use. The present invention provides for the effective and controlled insertion of foldable IOL's into eyes. Folding of such IOL's is also preferably easily achieved. The present system very conveniently provides for precise positioning of the IOL in the eye and controlled IOL release so as to reduce, or even eliminate, the risk of damaging the eye as a result of IOL insertion.

While this invention has been described with respect to various specific examples and embodiments, it is to be understood that the invention is not limited thereto and that it can be variously practiced within the scope of the following claims.

What is claimed is:

1. A method of inserting a foldable intraocular lens into the eye of a patient comprising:

holding a foldable intraocular lens with a forceps which can be moved between an open position and a closed position;

passing said held foldable intraocular lens distally in the bore of a tubular member having a distal end portion and an open distal end;

placing said distal end portion in proximity to or in the eye of the patient;

causing said foldable intraocular lens and at least a portion of said forceps to pass through said open distal end; and releasing said foldable intraocular lens from said forceps in the eye of the patient.

2. The method of claim 1 wherein said held foldable intraocular lens is in an unfolded state prior to being introduced into said tubular member.

3. The method of claim 1 wherein said held foldable intraocular lens is in a folded state prior to being introduced into said tubular member.

4. The method of claim 1 wherein said placing step causes said open distal end to be located outside the eye in proximity to an incision in the eye.

5. The method of claim 1 wherein said placing step causes said distal end portion to be located in the eye, and which further comprises withdrawing at least a part of said distal end portion from the eye prior to said releasing.

6. The method of claim 5 wherein said withdrawing causes only a part of said distal end portion to withdrawn from the eye prior to said releasing.

7. The method of claim 1 wherein said causing is effective to pass all of said foldable intraocular lens through said open distal end prior to said releasing.

8. The method of claim 1 which further comprises folding said foldable intraocular lens prior to introducing said foldable intraocular lens into said tubular member.

9. The method of claim 8 wherein said foldable intraocular lens is held by said forceps during said folding.

10. The method of claim 1 wherein said tubular member is tapered and has a proximal end portion which has a larger cross-sectional area than said distal end portion.

11. The method of claim 1 wherein said tubular member is structured to facilitate the folding of said foldable intraocular lens.

12. The method of claim 1 wherein said placing step further comprises placing said distal end portion in the eye.

* * * * *

UNITED STATES PATENT AND TRADEMARK OFFICE
CERTIFICATE OF CORRECTION

PATENT NO.   : 5,584,304
DATED        : December 17, 1996
INVENTOR(S)  : Brady

It is certified that error appears in the above-identified patent and that said Letters Patent is hereby corrected as shown below:

Column 3,
Line 19, "held. IOL" should read -- held IOL --.

Column 10,
Line 63, "to withdrawn" should read -- to withdraw --.

Signed and Sealed this

Twelfth Day of August, 2003

JAMES E. ROGAN
*Director of the United States Patent and Trademark Office*